(12) United States Patent
Peabody

(10) Patent No.: US 11,064,948 B2
(45) Date of Patent: Jul. 20, 2021

(54) MEDICAL DIAGNOSTIC DEVICE, SYSTEM, AND METHOD OF USE

(71) Applicant: Steven R. Peabody, Zionsville, IN (US)

(72) Inventor: Steven R. Peabody, Zionsville, IN (US)

( * ) Notice: Subject to any disclaimer, the term of this patent is extended or adjusted under 35 U.S.C. 154(b) by 427 days.

(21) Appl. No.: 16/090,585

(22) PCT Filed: Apr. 3, 2017

(86) PCT No.: PCT/US2017/025689
§ 371 (c)(1),
(2) Date: Oct. 1, 2018

(87) PCT Pub. No.: WO2017/173434
PCT Pub. Date: Oct. 5, 2017

(65) Prior Publication Data
US 2020/0229765 A1    Jul. 23, 2020

Related U.S. Application Data

(60) Provisional application No. 62/317,543, filed on Apr. 2, 2016.

(51) Int. Cl.
*A61B 5/00* (2006.01)
*G16H 40/67* (2018.01)
(Continued)

(52) U.S. Cl.
CPC ......... *A61B 5/6898* (2013.01); *A61B 5/0022* (2013.01); *A61B 5/02055* (2013.01);
(Continued)

(58) Field of Classification Search
CPC ..... H04W 12/033; G16H 40/67; G16H 10/60; G16H 15/00; G16H 50/70; G16H 80/00;
(Continued)

(56) References Cited

U.S. PATENT DOCUMENTS 6,942,518 B2   9/2005  Liamos et al.
2005/0010087 A1*  1/2005  Banet .................... G16H 40/67
                                                        600/300

(Continued)

FOREIGN PATENT DOCUMENTS

GB          2523880 A       9/2015

*Primary Examiner* — Eugene T Wu
(74) *Attorney, Agent, or Firm* — Roberts IP Law; John Roberts, Esq.

(57) ABSTRACT

Provided in various example embodiments a mobile device integrated in a body that is sized and shaped to be held in a palm of a hand of a user, the mobile device configured to take a plurality of physiological measurements of a patient, including electrocardiographic measurements, blood oxygen saturation level measurements, pulse rate measurements, body temperature measurements, blood pressure measurements when connected with a removable inflatable cuff, and blood glucose measurements when connected with an elongated test strip, and to display and wirelessly communicate data corresponding to said physiological measurements. The mobile device may comprise some or all of the features of an Internet enabled smartphone. The mobile device may be provided with selectable modes of operation for use with one or more patients. Wireless peripherals may provide additional physiological data to the device. Systems are provided for secure communication and storage of data.

18 Claims, 10 Drawing Sheets

(51) Int. Cl.
| | |
|---|---|
| *G16H 10/60* | (2018.01) |
| *G16H 15/00* | (2018.01) |
| *G16H 50/70* | (2018.01) |
| *G16H 80/00* | (2018.01) |
| *A61B 5/0205* | (2006.01) |
| *A61B 5/11* | (2006.01) |
| *A61B 5/145* | (2006.01) |
| *A61B 5/1455* | (2006.01) |
| *A61B 5/1477* | (2006.01) |
| *G01G 19/50* | (2006.01) |
| *G06Q 50/26* | (2012.01) |
| *A61B 5/282* | (2021.01) |
| *H04W 12/033* | (2021.01) |
| *A61B 5/022* | (2006.01) |
| *A61B 5/024* | (2006.01) |
| *G01S 19/42* | (2010.01) |
| *G01K 13/20* | (2021.01) |

(52) U.S. Cl.
CPC ........... *A61B 5/1112* (2013.01); *A61B 5/1117* (2013.01); *A61B 5/1118* (2013.01); *A61B 5/1477* (2013.01); *A61B 5/14532* (2013.01); *A61B 5/14552* (2013.01); *A61B 5/282* (2021.01); *A61B 5/6826* (2013.01); *A61B 5/746* (2013.01); *A61B 5/7445* (2013.01); *G01G 19/50* (2013.01); *G06Q 50/265* (2013.01); *G16H 10/60* (2018.01); *G16H 15/00* (2018.01); *G16H 40/67* (2018.01); *G16H 50/70* (2018.01); *G16H 80/00* (2018.01); *H04W 12/033* (2021.01); *A61B 5/02241* (2013.01); *A61B 5/02438* (2013.01); *G01K 13/20* (2021.01); *G01S 19/42* (2013.01)

(58) Field of Classification Search
CPC ...... G01G 19/50; G06Q 50/265; G01K 13/20; G01S 19/42; A61B 5/6898; A61B 5/282; A61B 5/0022; A61B 5/02055; A61B 5/1112; A61B 5/1117; A61B 5/1118; A61B 5/14532; A61B 5/14552; A61B 5/1477; A61B 5/6826; A61B 5/7445; A61B 5/746; A61B 5/02241; A61B 5/02438; A61B 5/0077; A61B 5/14551; A61B 5/6824; A61B 5/7275; A61B 5/318; A61B 5/7282; A61B 5/7405; A61B 5/01; A61B 5/6831
See application file for complete search history.

(56) References Cited

U.S. PATENT DOCUMENTS

| | | | |
|---|---|---|---|
| 2006/0202816 A1* | 9/2006 | Crump | G08B 21/0211 340/539.12 |
| 2007/0038136 A1 | 2/2007 | Gopinathan et al. | |
| 2008/0221930 A1* | 9/2008 | Wekell | H02J 7/0044 705/3 |
| 2008/0281168 A1* | 11/2008 | Gibson | A61B 5/14551 600/301 |
| 2009/0182205 A1* | 7/2009 | Cho | A61B 5/0261 600/301 |
| 2013/0090083 A1* | 4/2013 | DeMont | H04W 4/90 455/404.2 |
| 2014/0051941 A1* | 2/2014 | Messerschmidt | A61B 5/02416 600/301 |
| 2014/0058680 A1 | 2/2014 | Geva et al. | |
| 2014/0296669 A1 | 10/2014 | Gertsch et al. | |
| 2014/0371607 A1 | 12/2014 | Fitzsimmons et al. | |
| 2015/0201876 A1* | 7/2015 | Zhou | A61B 5/332 600/324 |
| 2015/0254414 A1 | 9/2015 | Patel | |

* cited by examiner

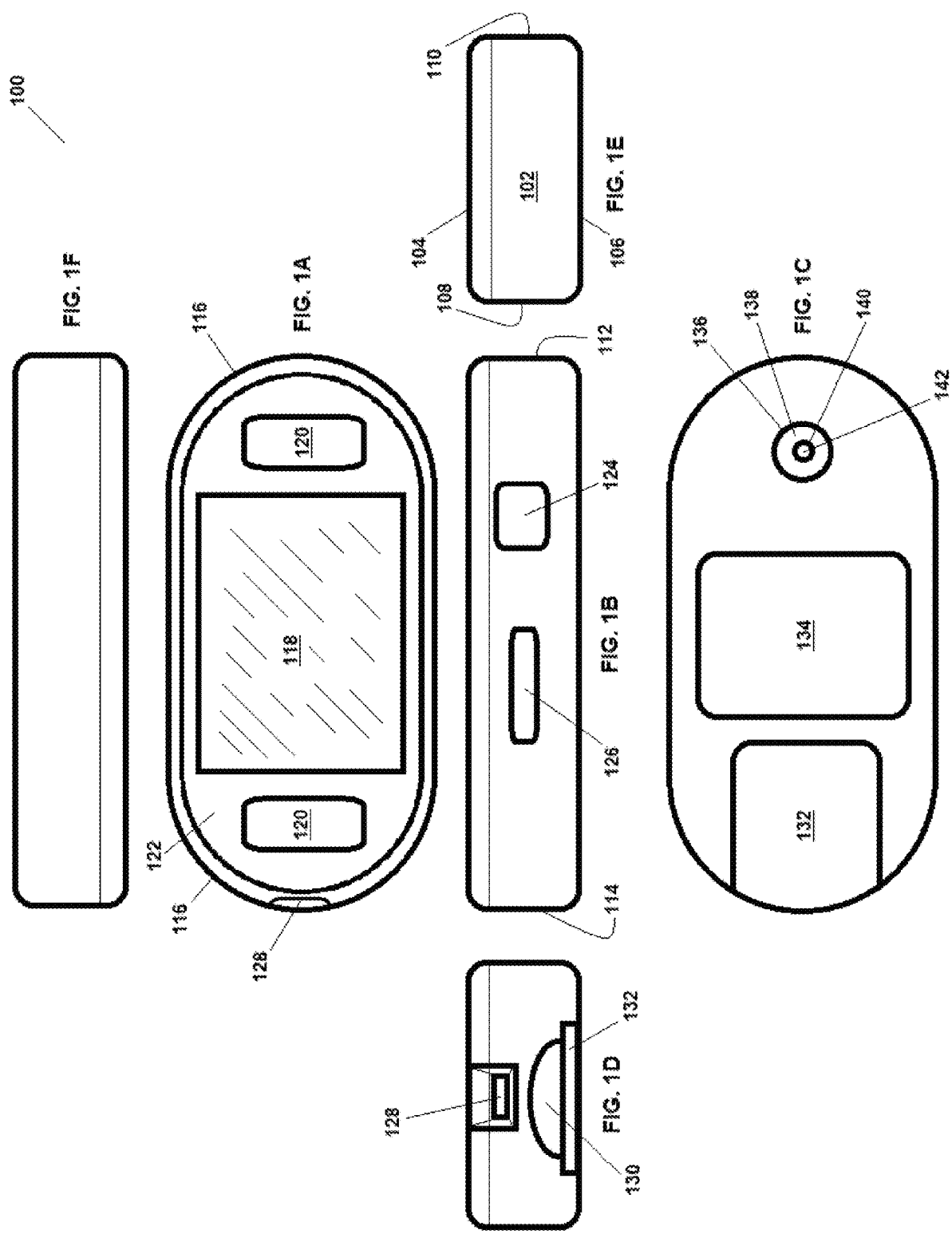

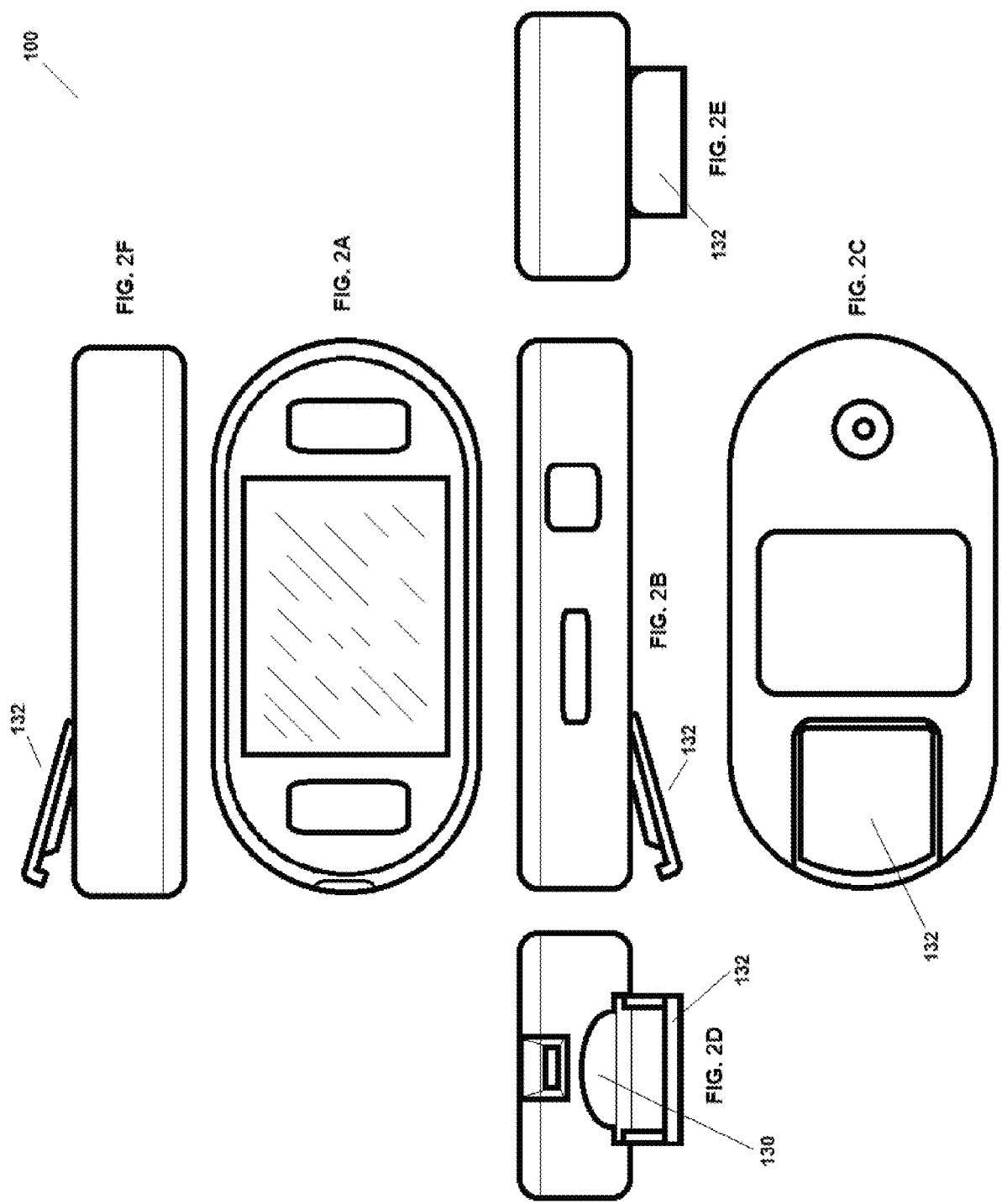

MEDICAL DIAGNOSTIC DEVICE, SYSTEM, AND METHOD OF USE

CROSS-REFERENCE TO RELATED APPLICATIONS

This application claims priority to and incorporates herein by reference international patent application PCT/US2017/025689 to Steven R. Peabody entitled Medical Diagnostic Device, System, and Method of Use, which was filed on Apr. 3, 2017 and published on Oct. 5, 2017 as WO 2017/173434 (herein "the PCT Application"). This application also claims priority to, incorporates herein by reference, and is a non-provisional of U.S. provisional patent application No. 62/317,543 to Steven R. Peabody, filed Apr. 2, 2016, entitled Medical Diagnostic Device, System, and Method of Use (herein "the '543 application").

FEDERALLY SPONSORED RESEARCH OR DEVELOPMENT

None.

TECHNICAL FIELD

The present invention relates to the field of diagnostic medicine and more particularly to a hand-held mobile medical diagnostic device and comprehensive remote patient telehealth monitoring system for measuring and wirelessly communicating a number of physiologic parameters.

BACKGROUND

Millions of elderly patients are cared for by home healthcare, nursing homes, and assisted living. According to The National Association for Home Care & Hospice, approximately twelve million individuals in the United States currently receive care from more than 33,000 agencies for causes including acute illness, long-term health conditions, permanent disability, or terminal illness. Additionally, there are millions of homebound and home-limited individuals who are unable to access the healthcare system due to combinations of functional impairment, chronic illness, and poverty. There is an urgent need for improved tools to help these persons obtain home health care more effectively and efficiently. In working to address these needs, innovations were discovered that have applicability to not only home health care but also to healthcare generally, and to health conscious individuals and those engaged in sports and exercise activities.

SUMMARY

Provided is a new treatment modality that consolidates into one hand-held device a multiplicity of medical measurement capabilities plus a hub for automatic wireless data transmission. In various example embodiments the hand-held device may be configured to measure and wirelessly communicate a plurality of physiologic parameters for one or more patients, including for instance any or all of blood pressure, blood glucose, body temperature, pulse rate, blood oxygen saturation level ($SpO_2$), and electrocardiogram (ECG). Additional peripheral devices may also be provided, either separately or along with the device as part of a kit, that automatically interface with and wirelessly transmit data to the hand-held device, such as fall detection, activity tracking, and smart scale peripherals. A carrying case may also be provided for the device, or for the device and one or more of its peripherals, either separately or along with the device as part of a kit. Also provided is an online network and interface for securely receiving, storing, compiling, and displaying data in a variety of formats selectively to patients, physicians, or other caretakers. The device and system simplify and improve management of multiple and often co-occurring chronic conditions such as diabetes, congestive heart failure, (CHF), chronic obstructive pulmonary disease (COPD), and hypertension, for example.

The device minimizes or eliminates human data entry errors since all readings are typically automatically uploaded after every use to a HIPAA-compliant (i.e., compliant with the Health Insurance Portability and Accountability Act of 1996) cloud network via cellular (e.g., 4G) and WiFi connectivity. Alternatively or additionally, the data can be sent directly to a provider's management solution directly through an application program interface (API). This replaces or minimizes the time-consuming and error-prone step of manually entering data, and patients no longer have to obtain and keep track of multiple devices. The device efficiently and effectively improves clinical outcomes, enhances patient engagement, and reduces total cost of care by reducing equipment costs, expanding the productivity of health care workers, and having patients self-report their medical data in an automatically accurate and timely fashion.

In various example embodiments the device may be configured to operate in a plurality of modes. For example, three modes might be provided, such as: guest or single test; point of care; and remote patient monitoring. In a guest mode, the device may operate as a stand-alone device providing visual indications of test results without communicating the test results to a network. In a point-of-care mode, the device may be configured to perform tests on and collect data separately for multiple patients whom may be at the same location (in the case of a hospital or care facility, for instance) or various different locations (in the case of a traveling nurse or other care provider, for instance), and to automatically and securely record and communicate the test result data, which may be time-stamped and GPS-location stamped, to a network. By automatically adding time and location data to the test data, an electronic audit trail is created that can be useful for validating care, avoiding insurance fraud, and ensuring standards of care are met.

A remote patient monitoring mode may be provided that may be configured to provide a single patient with a daily monitoring tool that is simple and easy enough for the patient to use on him or herself. The device may automatically collect and securely communicate test data, such as vital information, for example, to be viewed remotely by a doctor or other caregiver at their convenience without the need for manually logging, communicating, and compiling the data. In one example remote mode, patients can use a video communication feature to conduct telehealth visits directly through the device. The patient may also electronically pair various peripheral devices with the device to allow the device to passively collect and automatically communicate additional information, such as a fall detection device, wireless daily activity trackers, and a wireless smart weight scale, for example. Additionally, information can be entered manually through a touch-screen in certain example embodiments. Such pairing with such peripherals and manually entering data may optionally be used with other modes as well.

The present device is believed to be the first hand-held mobile medical device that comprises all the presentlydisclosed means for collecting medical data for diagnostics, and that also acts as its own wireless telecommunications hub that automatically uploads that data, for example as it is read to a HIPAA-compliant network on the cloud via 4G cellular and WiFi connectivity, in various example embodiments.

Accordingly, provided in various example embodiments is a mobile device integrated in a body that is sized and shaped to be held in a palm of a hand of a user. The mobile device may be configured to take a plurality of physiological measurements of a patient, who might or might not be the user in any particular circumstance, including electrocardiographic measurements, blood oxygen saturation level measurements, pulse rate measurements, body temperature measurements, blood pressure measurements when connected with a removable inflatable cuff, and blood glucose measurements when connected with an elongated test strip having at a first end an electrical connection point and at a second end an electrochemical cell. The mobile device may be configured to display and wirelessly communicate data corresponding to said physiological measurements.

In various example embodiments, the mobile device may comprise a display; a processor; a wireless modem with mobile broadband and GPS functionality; and a power source, such as a battery or a power cord. The mobile device may comprise a touch-screen data input structure and is configured to manually receive, display, and wirelessly communicate data corresponding to physiological measurements of the patient that were manually taken. The mobile device may comprise a cellular telephone; a camera, microphone, and speaker, all configured to allow the user to video-conference with one or more remotely-located persons. The mobile device may comprise two or more electrocardiographic electrodes integrated with and positioned on the body of the mobile device and configured to measure electrocardiographic signals of the patient when gripped by fingers or thumbs of the patient. The mobile device may comprise a fingertip pulse oximeter formed into the body of the mobile device and configured to measure pulse rate and blood oxygen saturation levels of the patient when a tip of a finger of the patient is inserted therein. The mobile device may comprise a temperature sensor integrated with and positioned on the body of the mobile device and configured to measure body temperature of the patient when the temperature sensor is placed against the patient's skin. The mobile device may comprise a blood pressure measuring structure within the body of the mobile device, comprising a controller, motor, pressure sensor, and pump in air communication with a tube interface at the body that is adapted to be removably and sealably connected with an inflatable cuff, which may be provided separately or along with the mobile device as part of a kit. The mobile device may comprise a blood glucose measuring structure within the body of the mobile device, comprising an electrical connector at the body, wherein the electrical connector disposed to form an electrical connection with the electrical connection point on the first end of the elongated test strip, when the elongated strip is inserted in the electrical connector. Such test strips may be provided separately and/or along with the mobile device as part of a kit.

In various example embodiments the mobile device may be configured to automatically wirelessly communicate to a network said data corresponding to said physiological measurements. The mobile device may be configured to wirelessly receive, display, and wirelessly communicate data corresponding to physiological measurements taken by a peripheral device not physically connected to the mobile device. The peripheral devices may include a scale configured to measure and wirelessly communicate data corresponding to the weight of the patient; a fall detection device configured to be worn by the patient and to detect and to wirelessly communicate data indicating when the patient has fallen; and an activity tracker configured to be worn by the patient and to measure and wirelessly communicate data corresponding to an amount of physical activity engaged in by the patient over a period of time. The mobile device may be configured to communicate with and display information from the Internet. The mobile device may be configured to wirelessly communicate an alert to the user, and optionally to someone located remotely from the user, when said data corresponding to said physiological measurements exceeds a predetermined threshold.

The mobile device may be configured to be selectably operable in a plurality of modes. For example, in a first mode the mobile device may be configured to display visual indications of data corresponding to said physiological measurements without communicating said data wirelessly. In a second mode the mobile device may be configured to display visual indications of data corresponding to said physiological measurements and to associate with said data a patient identifier, time stamp, and GPS location, and to automatically wirelessly communicate said data for each patient securely to a network. In a third mode the mobile device may be configured to display visual indications of data corresponding to said physiological measurements and to automatically wirelessly communicate said data securely to a network. In such a third mode the mobile device may be further configured to automatically wirelessly communicate securely to a network data corresponding to physiological measurements taken by one or more peripheral devices not physically connected to the mobile device. In a third mode the mobile device may be configured to allow the patient to communicate with remotely located persons by audio and video.

Also provided in various example embodiments is a system comprising a plurality of mobile devices as described herein, for use with a plurality of patients, all in wireless communication with a remotely-located computer network configured to securely receive, store, compile, and selectively display in a plurality of formats the data corresponding to the physiological measurements of the patients. The formats may include a single-patient format where the data corresponding to the physiological measurements corresponds to a single one of the patients. The formats may also include a multiple-patient format where the data corresponding to the physiological measurements corresponds to a plurality of the patients.

The foregoing summary is illustrative only and is not meant to be exhaustive or limiting. Other aspects, objects, and advantages of various example embodiments will be apparent to those of skill in the art upon reviewing the accompanying drawings, disclosure, and appended claims. These together with other objects of the invention, along with various features of novelty, which characterize the invention, are pointed out with particularity in the claims annexed hereto and forming a part of this disclosure. For a better understanding of the invention, its operating advantages and the specific objects attained by its uses, reference should be had to the accompanying and incorporated drawings, claims, and descriptive matter in which there is illustrated one or more non-limiting preferred embodiments.

BRIEF DESCRIPTION OF THE DRAWINGS

FIGS. 1A-1F illustrate certain aspects of an example mobile device integrated in a body that is sized and shaped to be held in a palm of a hand of a user, according to certain example embodiments, wherein:

FIG. 1A is a top plan view thereof;
FIG. 1B is a front side elevation view thereof;
FIG. 1C is a bottom plan view thereof;
FIG. 1D is a left side elevation view thereof;
FIG. 1E is a right side elevation view thereof; and
FIG. 1F is a back side elevation view thereof.

FIGS. 2A-2F illustrate certain aspects of the example mobile device of FIG. 1A, showing an example fingertip pulse oximeter in an open position so that a tip of a finger of a patient may be inserted therein, according to certain example embodiments, wherein:

FIG. 2A is a top plan view thereof;
FIG. 2B is a front side elevation view thereof;
FIG. 2C is a bottom plan view thereof;
FIG. 2D is a left side elevation view thereof;
FIG. 2E is a right side elevation view thereof; and
FIG. 2F is a back side elevation view thereof.

In the following description, like reference numbers from the figures may be used to refer to like elements and features in connection with various different embodiments.

DETAILED DESCRIPTION OF EXAMPLE EMBODIMENTS

Figure 1G:
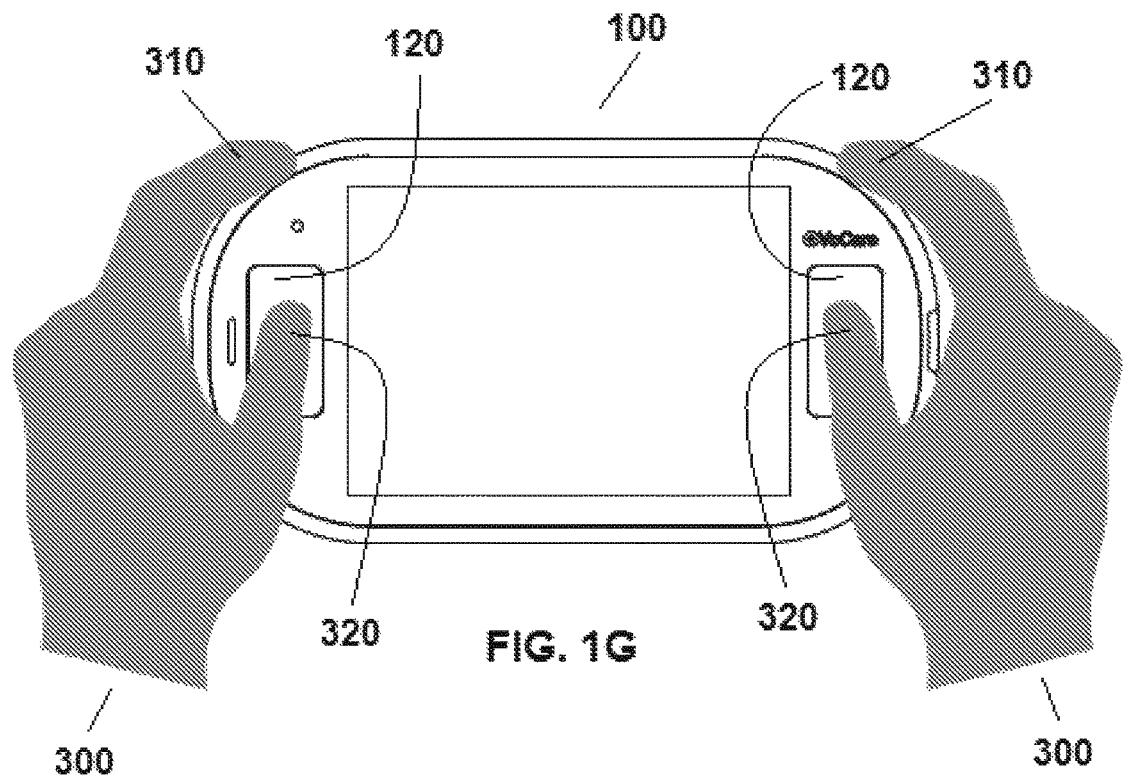
FIG. 1G is a top plan view of another example mobile device integrated in a body that is sized and shaped to be held in a palm of a hand of a user, illustrating a patient taking an ECG measurement by placing their thumbs on ECG sensors on the device, according to certain example embodiments.
Figure 1H:
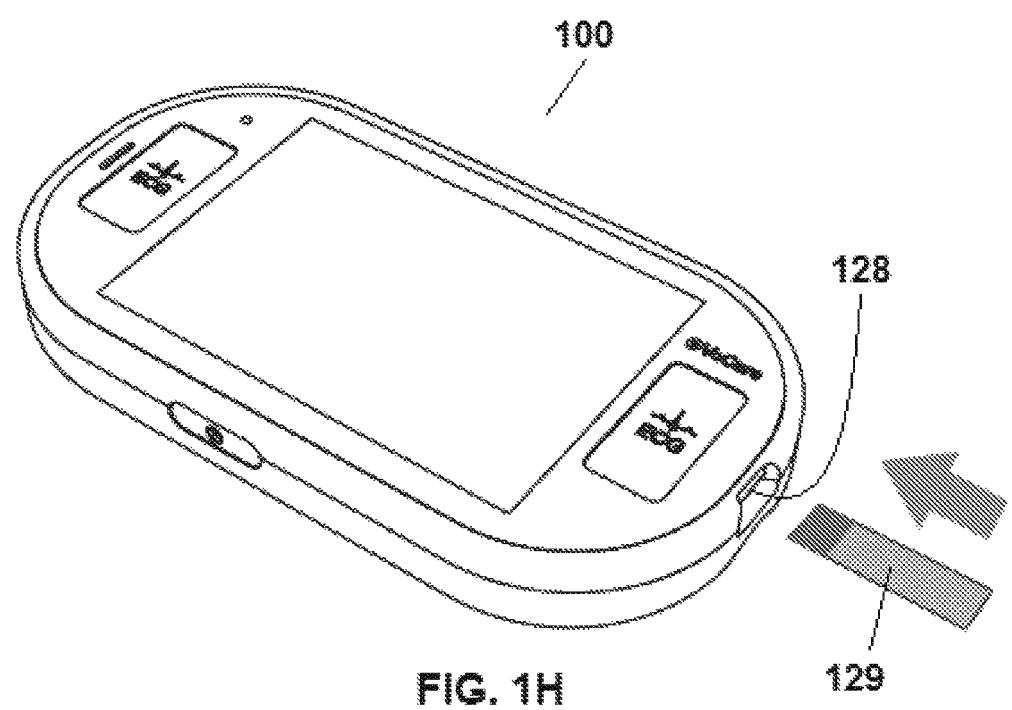
FIG. 1H is a top perspective view of the example mobile device of FIG. 1G, illustrating a test strip being inserted into a glucometer portion of the device, according to certain example embodiments.

Reference will now be made in detail to some specific example embodiments, including any best mode contemplated by the inventor. Examples of these specific embodiments are illustrated in the accompanying drawings. While the invention is described in conjunction with these specific embodiments, it will be understood that it is not intended to limit the invention to the described or illustrated embodiments. On the contrary, it is intended to cover alternatives, modifications, and equivalents as may be included within the spirit and scope of the invention as defined by the appended claims.

In the following description, numerous specific details are set forth in order to provide a thorough understanding of the present invention. Particular example embodiments may be implemented without some or all of these features or specific details. In other instances, components and procedures well known to persons of skill in the art have not been described in detail in order not to obscure inventive aspects.

Various techniques and mechanisms will sometimes be described in singular form for clarity. However, it should be noted that some embodiments may include multiple iterations of a technique or multiple components, mechanisms, and the like, unless noted otherwise. Similarly, various steps of the methods shown and described herein are not necessarily performed in the order indicated, or performed at all in certain embodiments. Accordingly, some implementations of the methods discussed herein may include more or fewer steps than those shown or described.

Further, the example techniques and mechanisms described herein will sometimes describe a connection, relationship or communication between two or more items or entities. It should be noted that a connection or relationship between entities does not necessarily mean a direct, unimpeded connection, as a variety of other entities or processes may reside or occur between any two entities. Consequently, an indicated connection does not necessarily mean a direct, unimpeded connection unless otherwise noted.

Referring now to the drawings in detail wherein like elements are indicated by like numerals, FIGS. 1A through 1F depict an example embodiment of a mobile device 100 integrated in a body 102 that is sized and shaped to be held in a palm of a hand of a user, for instance as depicted in the photographs in the '543 application. The mobile device 100 may be configured to take a plurality of physiological measurements of a patient (depicted in the photographs in the '543 application), who might or might not be the user in any particular circumstance. For example, a nurse or other healthcare provider may in some cases use the device 100 on one or more patients. In other cases the patient may use the device 100 on him or herself.

The body 102 of the mobile device 100 may comprise a top portion 104, a bottom portion 106, a front portion 108, a back portion 110, a right portion 112 and a left portion 114. In various example embodiments, the mobile device 100 may comprise a display 118, such as a touch-screen display used on a smartphone. Inside the body 102 of the device 100 may be a processor, wireless modem with mobile broadband and GPS functionality, and a power source, such as a battery or a power cord. For example, regarding the built-in wireless hub and GPS aspects of the device 100, these may in certain example embodiments be provided by incorporating within the body of the device 100 a LTE/EV-DO/HSPA+ Qualcomm® Gobi™ 4G Module, for example. Such a module may be provided with the following specifications and capabilities, for example:

LTE: 1900 (Band 2), 1700/2100 (Band 4), 850 (Band 5), 700 (Band 13), 700 (Band 17), 1900 (Band 25) MHz;

HSPA+: 2100 (Band 1), 1900 (Band 2), AWS 1700/2100 (Band 4), 850 (Band 5), 800 (Band 8) MHz E-GPRS: 1900 (Band 2), 1800 (Band 3), 850 (Band 5), 900 (Band 8) MHz;

EV-DO: 800 (BC0), 1900 (BC1) MHz;

3GPP Release 8 LTE Specification;

WCDMA R99, 3GPP Release 5, 6 and 7 UMTS Specification EVDO Release 0 and Release A;

Standalone GPS, A-GPS, GPS XTRA;

1575.42 MHz (±1.023 MHz), GLONASS 1596-1607 MHz;

LTE (Category 3): 100 Mbps (Download), 50 Mbps (Upload) DC-HSPA+: 42 Mbps (Download), 5.76 Mbps (Upload) HSPA+: 21.6 Mbps (Download), 5.76 Mbps (Upload);

EDGE: 236.8 kbps (Download), 236.8 kbps (Upload) GPRS: 85.6 kbps (Download), 85.6 kbps (Upload);

LTE: +23 dBm;

WCDMA: +23 dBm;

GSM 850/900, GMSK: +32 dBm;

GSM 850/900, 8PSK: +27 dBm DCS1800/PCS 1900, GMSK: +29 dBm DCS1800/PCS 1900, 8PSK: +26 dBm CDMA: +24 dBm;

LTE: 1,200 mA (peak); 900 mA (average) WCDMA: 1,100 mA (peak); 800 mA (average) EGPRS: 2,500 mA (peak); 700 mA (average);

Bluetooth 4.2;

IEEE 802.15.1; and

WiFi 802.11ac.

The latest version of Wi-Fi, Wi-Fi CERTIFIED ac, offers healthcare facilities a significant performance leap, without sacrificing core competencies like interoperability, security and ease of use. Wi-Fi CERTIFIED devices are backward compatible, so newer devices will seamlessly interoperate with current devices. Wi-Fi CERTIFIED ac devices are also expected to include Wi-Fi CERTIFIED n, and dual-band networks will enable more capacity, higher throughput, better coverage and lower latency in healthcare environments.

The mobile device 100 may comprise a touch-screen data input structure 118 and is configured to manually receive, display, and wirelessly communicate data corresponding to physiological measurements of the patient that were manually taken. The mobile device 100 may comprise a cellular telephone within the body 102, comprising a camera and microphone, for instance on surface 122 of the upper portion 104 of the body 102, and a speaker, for instance in area 126 of the front portion 108 of the body 102, all configured to allow the user to video-conference with one or more remotely-located persons. Area 126 may also be used for plugs of various types, for instance to charge the device 100. A power on-off button may be provided, for instance at location 124. In these respects the mobile device 100 may comprise any or all of the features of a typical smartphone.

With reference to FIGS. 1A through 1H, The mobile device 100 may comprise two or more electrocardiographic electrodes 120 integrated with and positioned on the body 102 of the mobile device 100 and configured to measure electrocardiographic signals of the patient 300 when gripped by fingers 310 or thumbs 320 of the patient. The electrocardiographic electrodes or ECG sensors 120 may be placed on the upper surface 104 as shown in FIG. 1A, or may be placed on a different surface in other embodiments. The electrocardiographic electrodes or ECG sensors 120 may be thumb ECG signal recorders and make use of standard ECG measurement principles. That is, the electrical changes which are caused by heart muscle activity are measured via the skin. Instead of using electrodes connected to chest and extremities, a user connects to the electrode by placing the thumbs on two electrode patch areas integrated on the device 100. Referring to standard ECG terminology, a single lead measurement setup may be achieved. Incorporated herein by reference is United States published patent application US 20140073979 A1 to Inciardi et al., entitled eCard ECG Monitor and published on Mar. 13, 2014. The ECG system may be adapted for home, office, and travel use by the general public with or without a physician prescription. It can also be used by physicians and other health-related personnel conducting recordings on their patients while with them. The ECG system records for periods of time chosen by the user, with the record then available for review or subsequent analysis, printing, saving, and sending. For example, this ECG data may be displayed on the display 118 and may be tracked by the device 100 and transmitted wirelessly by the device 100 remotely to a network, or directly to a physician or other caregiver directly from the device 100, for instance by email, text, or other means, either automatically or by operation of the user. Besides showing the ECG waveform on the screen 118, the screen or ECG monitor 118 may be configured to display various measurements, such as heart rate, and an interpretation of the reading, such as normal, irregular heart rhythm, occasionally double heartbeat period, bradycardia, and the like.

The mobile device 100 may comprise a temperature sensor 134 integrated with and positioned on the body 102 of the mobile device 100 and configured to measure body temperature of the patient when the temperature sensor 134 is placed against the patient's skin (or in other embodiments, sufficiently near the patient's skin). The temperature sensor 134 may be placed on the bottom surface 106 as shown in FIG. 1C, or may be placed on a different surface in other embodiments. Regarding the thermometer of the device 100, it may be a conventional forehead thermometer that has an infrared detecting unit 134. When placed against or sufficiently near the forehead of the patient (depicted in the photographs in the '543 application), the infrared detecting unit 134 may be configured to receive the infrared energy radiated from the forehead of a patient and transmits the detecting result to a computing unit of the device 100 to compute and convert the infrared energy into temperature to estimate a forehead temperature or a core temperature of a human body. This temperature data may then be displayed on the display 118 and may be tracked by the device 100 and transmitted wirelessly by the device 100 remotely to a network, or directly to a physician or other caregiver directly from the device 100, for instance by email, text, or other means, either automatically or by operation of the user. In certain example embodiments the thermometer has a measuring range from 32° C. (89.6° F.) to 43° C. (109.4° F.), with an accuracy of ±1° F. Incorporated herein by reference is United States published patent application US 2015/0168233 A1 to Ho, entitled Forehead Thermometer and published Jun. 18, 2015; United States published patent application US 20150043613 A1 to Tanaka, entitled Infrared Thermometer and published Feb. 12, 2015; and U.S. Pat. No. 6,292,685 to Pompei, entitled Temporal Artery Temperature Detector and issued Sep. 18, 2001.

With reference to FIGS. 1A through 1K, the mobile device 100 may comprise a blood pressure measuring structure within the body 102 of the mobile device, comprising a controller, motor, pressure sensor, and pump in air communication with a tube interface 136, 138, 140, 142 at the body 102 that is adapted to be removably and sealably connected with an inflatable cuff 150 (depicted in FIGS. 1i-1K and in the photographs in the '543 application), which may be provided separately or along with the mobile device 100 as part of a kit. In various example embodiments blood pressure measurements may be taken with the oscillometric method with automatic inflation and controlled pressure release valve. Incorporated herein by reference are United States published patent application US 2014/0371607 A1 to Fitzsimmons et al., entitled Devices And Methods For Measuring Blood Pressure and published Dec. 18, 2014 ("the '607 Publication"); and United States published patent application US 2007/0093718 A1 to Lane et al., entitled Modular Blood Pressure Measurement Apparatus and published Apr. 26, 2007 ("the '718 Publication").

The tube interface 136, 138, 140, 142 may be placed on the bottom surface 106 as shown in FIG. 1C, or may be placed on a different surface in other embodiments. In this particular example embodiment, the tube interface comprises a recessed annular area 138 defined by a sidewall 136 extending inward from the bottom 106 of the body 102. A hose coupling 140 extends outward from the recessed annular area 138 but without extending beyond the bottom 106 of the body 102. The hose coupling 140 may be a nipple or other structure configured to removably and sealably attach with a hose or other coupling 170 on an inflatable blood pressure cuff 150, such that the cuff 150 can be in air communication from its coupling 170 through an opening 142 in the coupling 140 in the device 100.

An inflatable arm cuff 150 may be provided along with the device 100 as part of a kit, the arm cuff 150 having a hose or fitting 170 that is configured to removably and sealably attach to connector 140 on the device 100 so that the pump and other blood pressure measuring means within the device 100 is in air flow and air pressure communication with the arm cuff 150. In various example embodiments the arm cuff 150 may be configured to fit upper arm circumferences in the nine inch to seventeen inch range. Alternatively, a cuff 150 may be provided that is configured for use with a patient's wrist, for example as provided in U.S. Pat. No. 5,687,732 A to Inagaki et al., entitled Blood Pressure Monitor and issued Nov. 18, 1997 ("the '732 patent"), which is incorporated herein by reference. Also incorporated herein by reference is U.S. Pat. No. 5,022,403 A to LaViola, entitled Automatic Blood Pressure Measuring Device And Method With Cuff Size Determination and issued Jun. 11, 1991 ("the '403 patent").

Figure 1I:
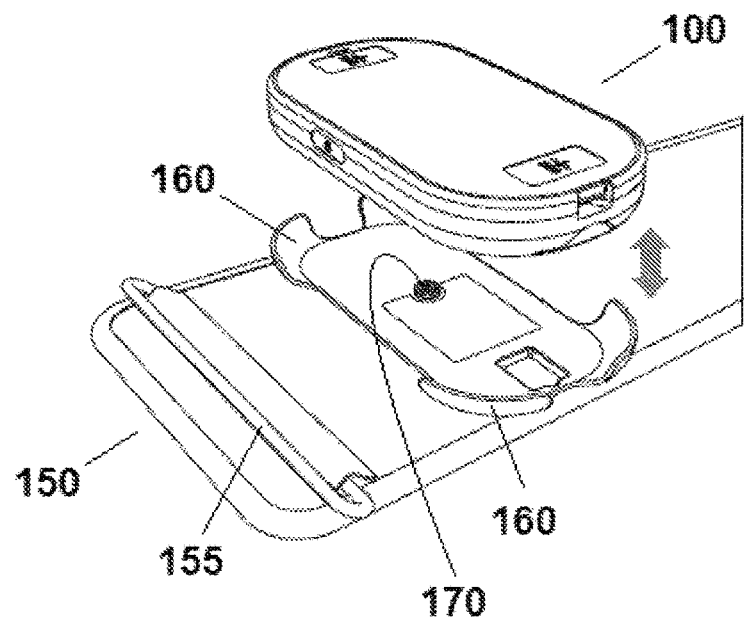
FIG. 1i illustrates the example mobile device of FIG. 1G being removably attached with an example inflatable blood pressure cuff according to various example embodiments.
Figure 1J:
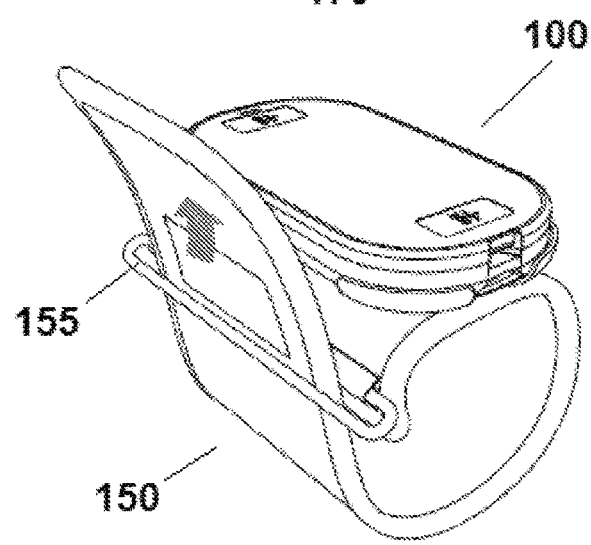
FIG. 1J illustrates the example mobile device of FIG. 1G removably attached with the example inflatable blood pressure cuff of FIG. 1i, and further illustrates the example blood pressure cuff being pulled through a buckle according to various example embodiments.
Figure 1K:
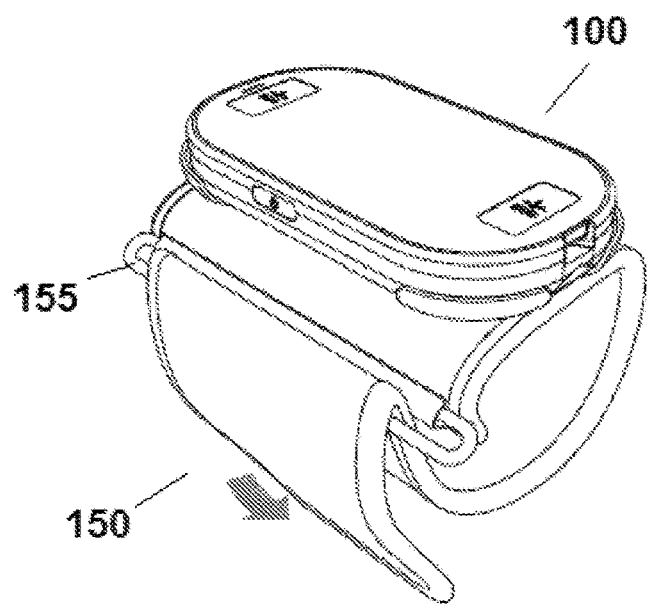
FIG. 1K illustrates the example mobile device of FIG. 1G removably attached with the example inflatable blood pressure cuff of FIG. 1i, and further illustrates the example blood pressure cuff being fastened around the buckle according to various example embodiments.

With reference to FIGS. 1i through 1K, arm cuff 150 may be provided with a structure 160 that is sized and shaped to removably connect the device 100 to the cuff 150. For example, a resilient plastic or metal housing clip structure 160 may be attached to cuff 150 proximate hose or fitting 170 that comprises projections extending away from the cuff 150 that are sized and shaped to snap-on to the outer surface 116 (FIG. 1A) of the device 100, similar to clips that removably hold mobile phones. Such a clip structure 160 can hold the device 100 in place on the cuff 150 while blood pressure measurements are taken, while also positioning the device 100 properly for connection of the coupling 140 of the device 100 with the corresponding hose, fitting, or coupling 170 on the cuff 150.

With continuing reference to FIGS. 1i through 1K, arm cuff 150 may be provided with a buckle 155 that facilitates quick assembly of the cuff 150 onto and off of the arm of a patient, as shown by the arrows in the figures. Portions of the cuff 150 may be provided with hook and loop fastening material (not shown) to secure the cuff 150 at the proper tightness on the arm of a patient, and to provide for easy and quick removal.

Examples of the blood pressure monitor structure in device 100 have been clinically validated to accurately measure a patient's systolic and diastolic blood pressure along with the patient's heart rate. A triple measurement average may be taken for the most precise feedback. In certain example embodiments of the device 100 the blood pressure measurement structure had a measurement range of 40~250 mmHg for blood pressure and 40~200 beats per minute for pulse, with measurement accuracy of ±3 mmHg or ±2% of readout value for blood pressure, and ±5% of readout for pulse, and measurement resolution of 1 mmHg for blood pressure and 1 beat/min for pulse. This blood pressure data may be displayed on the display 118 and may be tracked by the device 100 and transmitted wirelessly by the device 100 remotely to a network, or directly to a physician or other caregiver directly from the device 100, for instance by email, text, or other means, either automatically or by operation of the user.

In alternative embodiments the device 100 may measure blood pressure using technology other than an inflatable cuff or sphygmomanometer. For example, the device 100 may comprise, within the body, surface acoustic wave (SAW) technology for measuring blood pressure. Incorporated herein by reference is United States published patent application US 20110208066 A1 to Gnadinger, entitled Noninvasive Blood Pressure Measurement and Monitoring Device and published Aug. 25, 2011 ("the '066 Publication").

With reference to FIGS. 1A through 1F and 1H, The mobile device 100 may comprise a blood glucose measuring structure within the body 102 of the mobile device 100, comprising an electrical connector 128 at the body 102. The electrical connector 128 may be formed into a recessed area on the upper left side 114 of the body 102 as shown in FIGS. 1D and 1A, or may be located on a different surface in other embodiments. The electrical connector 128 is disposed to form an electrical connection with the electrical connection point on the first end of a typical elongated test strip 129 (depicted in the FIG. 1H and the photographs in the '543 application), when the elongated strip 129 is inserted in the electrical connector 128. Such test strips 129 may be provided separately or along with the mobile device 100 as part of a kit. Test results from capillary blood samples taken using test strips 129 plugged into electrical connector 128 have shown excellent correlation to reference samples, meeting the ISO accuracy acceptance criteria of ±15 mg/dL for results. Incorporated herein by reference are United States published patent application US 2005/0265094 A1 to Harding et al., entitled Measuring Device And Methods For Use Therewith and published Dec. 1, 2005 ("the '094 Publication"); United States published patent application US 2012/0302853 A1 to Chen et al., entitled System And Method For Measuring Physiological Parameters and published Nov. 29, 2012 ("the '853 Publication"); and United States published patent application US 2010/0249965 A1 to Rao et al., entitled Integrated Blood Glucose Measurement Device and published Sep. 30, 2010 ("the '965 Publication"). This blood glucose data may be displayed on the display 118 and may be tracked by the device 100 and transmitted wirelessly by the device 100 remotely to a network, or directly to a physician or other caregiver directly from the device 100, for instance by email, text, or other means, either automatically or by operation of the user.

Figure 2G:
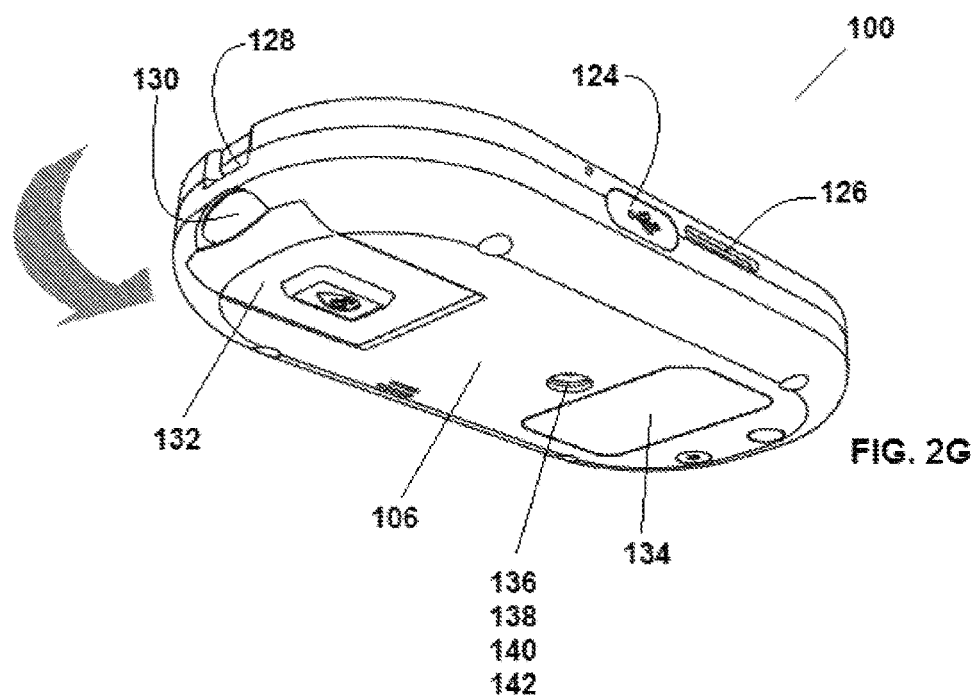
FIG. 2G is a bottom perspective view of another example mobile device integrated in a body that is sized and shaped to be held in a palm of a hand of a user, according to certain example embodiments, with an arrow indicating the direction to open an example fingertip pulse oximeter.
Figure 2H:
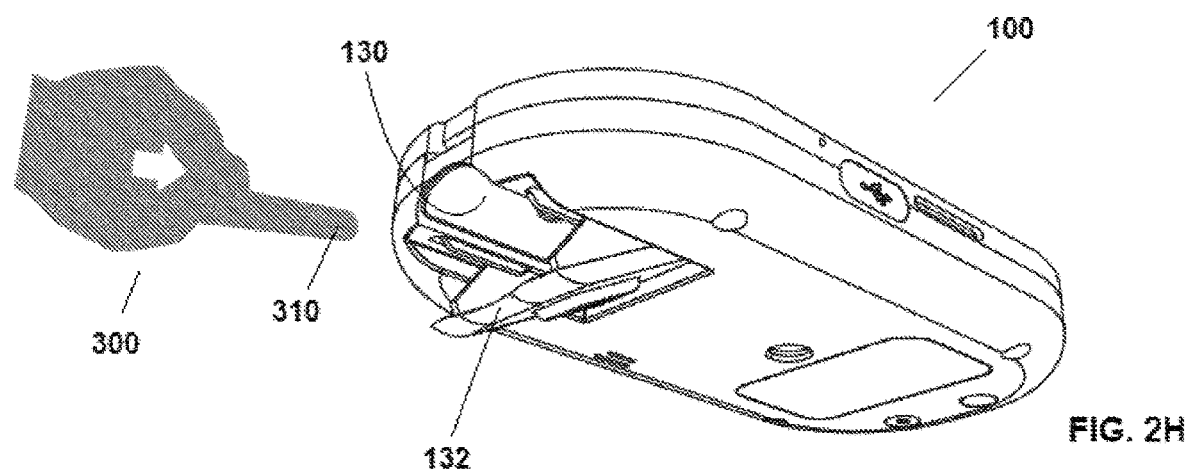
FIG. 2H is a bottom perspective view of the example mobile device of FIG. 2G, showing the example fingertip pulse oximeter in an open position and illustrating a patient beginning to insert their fingertip therein, according to certain example embodiments.

With reference to FIGS. 1A-1F as well as FIGS. 2A-2H, the mobile device 100 may comprise a fingertip pulse oximeter 130 formed into the body 102 of the mobile device 100 and configured to measure pulse rate and blood oxygen saturation levels of the patient when a tip 310 of a finger of the patient 300 is inserted into the fingertip pulse oximeter 130, for instance as depicted in the photographs in the '543 application and in FIG. 2H. The fingertip pulse oximeter 130 may be formed into a recessed, concave-contoured area 130 extending into the lower left side 114 of the body 102 as shown in FIG. 1D, or may be located on a different surface in other embodiments. The fingertip pulse oximeter 130 may be provided with a hingeably mounted portion 132 forming part of the lower surface 106 of the body 102 as shown in FIGS. 1C, 1D, and 2G. As shown in FIGS. 2B-2H, the hingeably mounted portion 132 may pivot open to allow space for the patient to insert a tip of their finger into the fingertip pulse oximeter 130, for instance as depicted in the photographs in the '543 application and in FIG. 2H. The sensor for the fingertip pulse oximeter 130 may be of the conductive type, for instance as disclosed in U.S. Pat. Nos. 5,279,295; 5,035,243; 5,217,012; 5,249,576; 5,246,003; 5,209,230; 5,170,786; 5,080,098; 5,069,213; 5,041,187; 4,971,062; 4,964,408; 4,928,691; 4,865,038; 4,830,014; 4,825,879; 4,825,872; 4,770,179; 4,700,708; 4,653,498, and 4,621,643, all of which are incorporated herein by reference. Alternatively, the sensor for the fingertip pulse oximeter 130 may be of the transmissive type, for example as disclosed in U.S. Pat. No. 5,792,052 A to Isaacson et al., entitled Finger Clip Pulse Oximeter and issued Aug. 11, 1998 ("the '052 patent"), which is incorporated herein by reference. In certain example embodiments of the device 100 the fingertip pulse oximeter measurement structure has had a range of measured saturation percentage of $O_2$ ($SpO_2$) from 50 to 100 with accuracy within 2% from 75.0-100, and 3% from 50-74.9, and measured pulse rate from 25 to 240 beats per minute (bpm). This saturation percentage and heart rate data may be displayed on the display 118 and may be tracked by the device 100 and transmitted wirelessly by the device 100 remotely to a network, or directly to a physician or other caregiver directly from the device 100, for instance by email, text, or other means, either automatically or by operation of the user.

In certain example embodiments the user may manually enter data, such as identifying information, height, weight, age, etc., through a touch-screen display 118, or via any other means, such as by voice-recognition software or by causing such information to be wirelessly communicated to the device 100.

Additional or different measuring means for different or additional physiological parameters may be provided in various example embodiments. In certain example embodiments fewer than all of the above measurement means may be incorporated into a device 100. The invention is not necessarily limited to devices 100 having all six of the physiological measurement means described herein; other devices may have five, four, three, two, or just one of the measurement means described herein. Likewise, it is contemplated that additional physiological measurement means may be incorporated into the device 100, such as a breathalyzer, for example. All such embodiments fall within the scope of the present invention as defined by any claims issued in this application or a child of this application.

Figure 3:
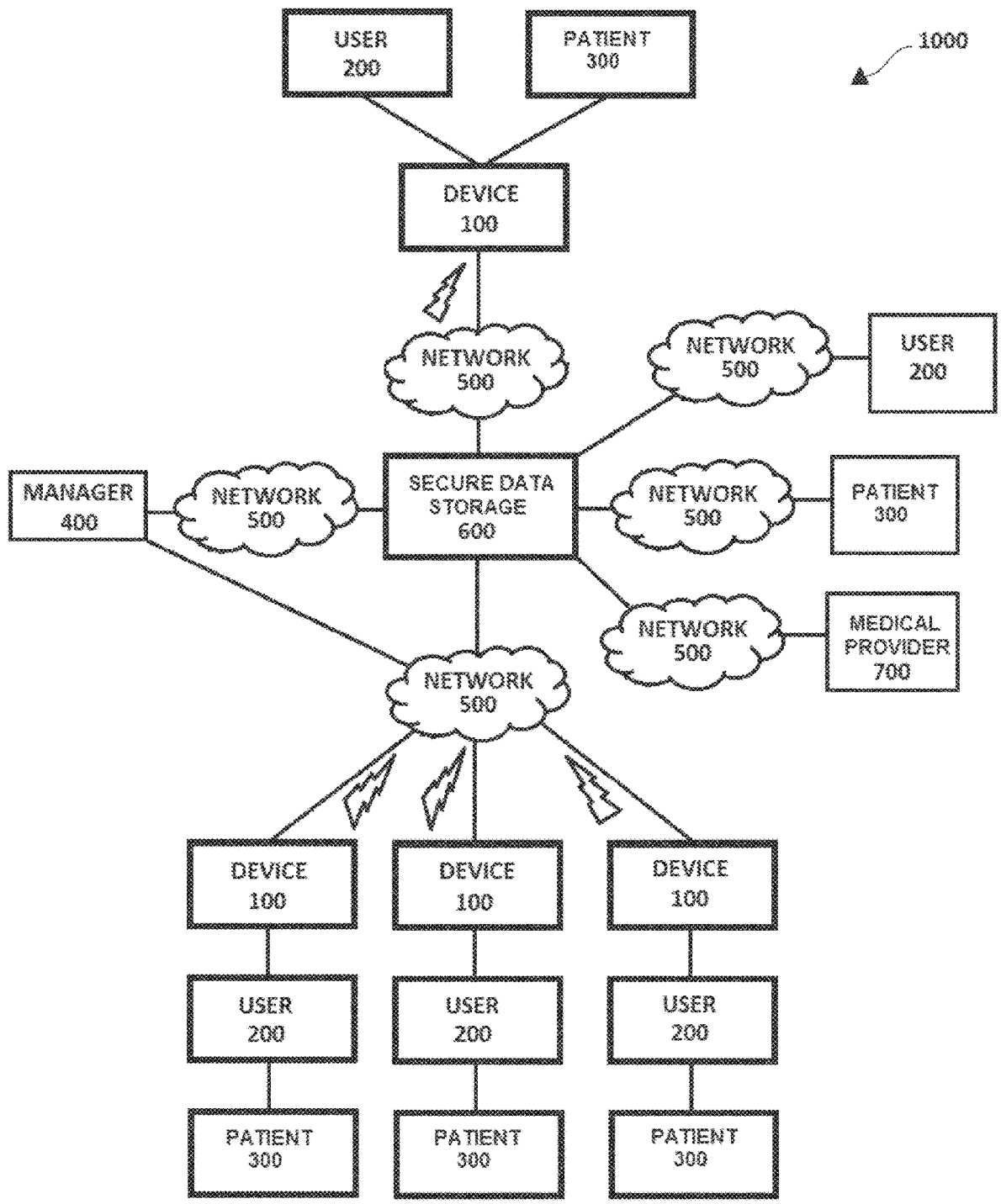
FIG. 3 is a diagram of an example system according to various example embodiments, depicting the example system operating in a first non-limiting example modality.
Figure 4:
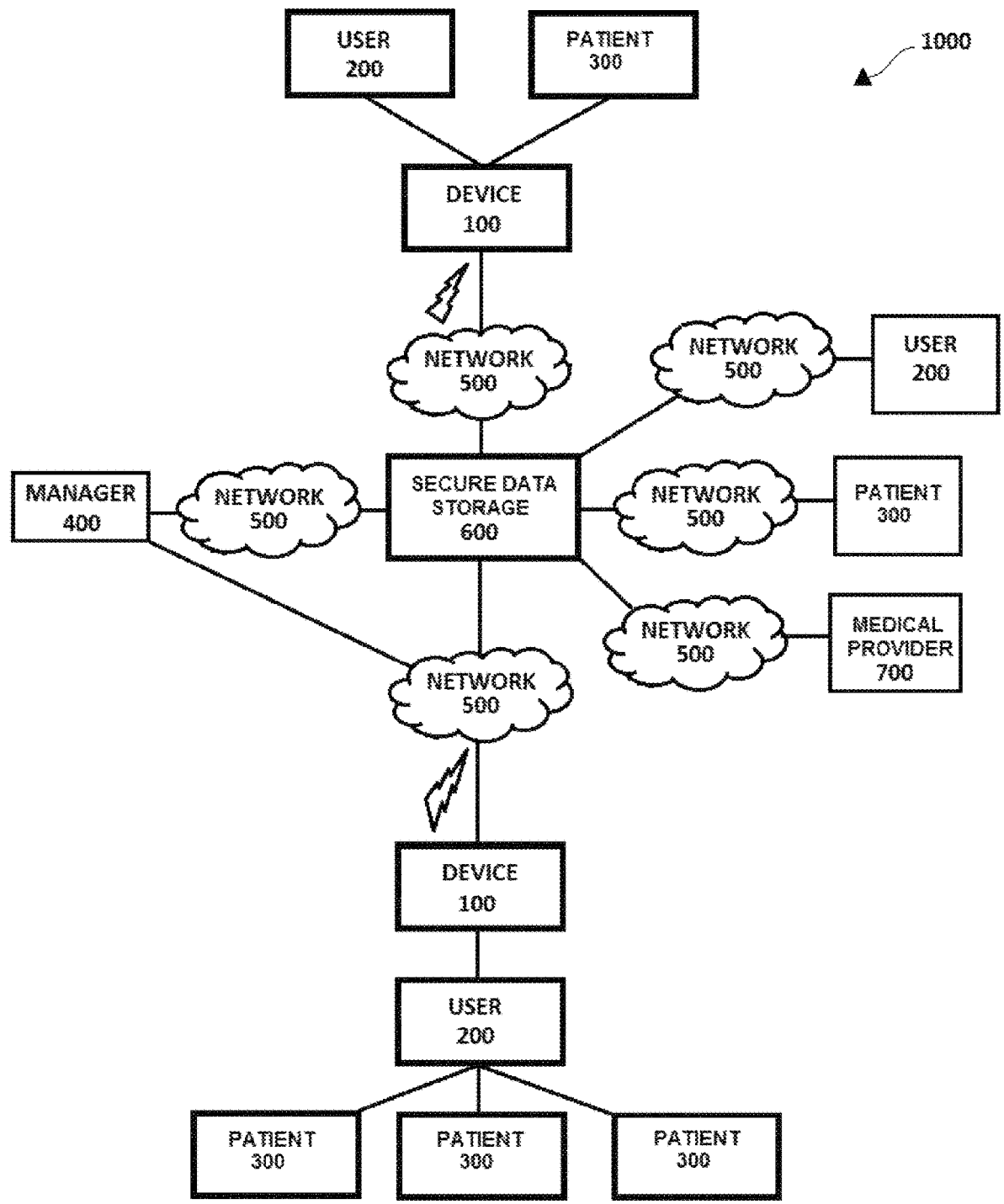
FIG. 4 is a diagram of an example system according to various example embodiments, depicting the example system operating in a second non-limiting example modality.
Figure 5:
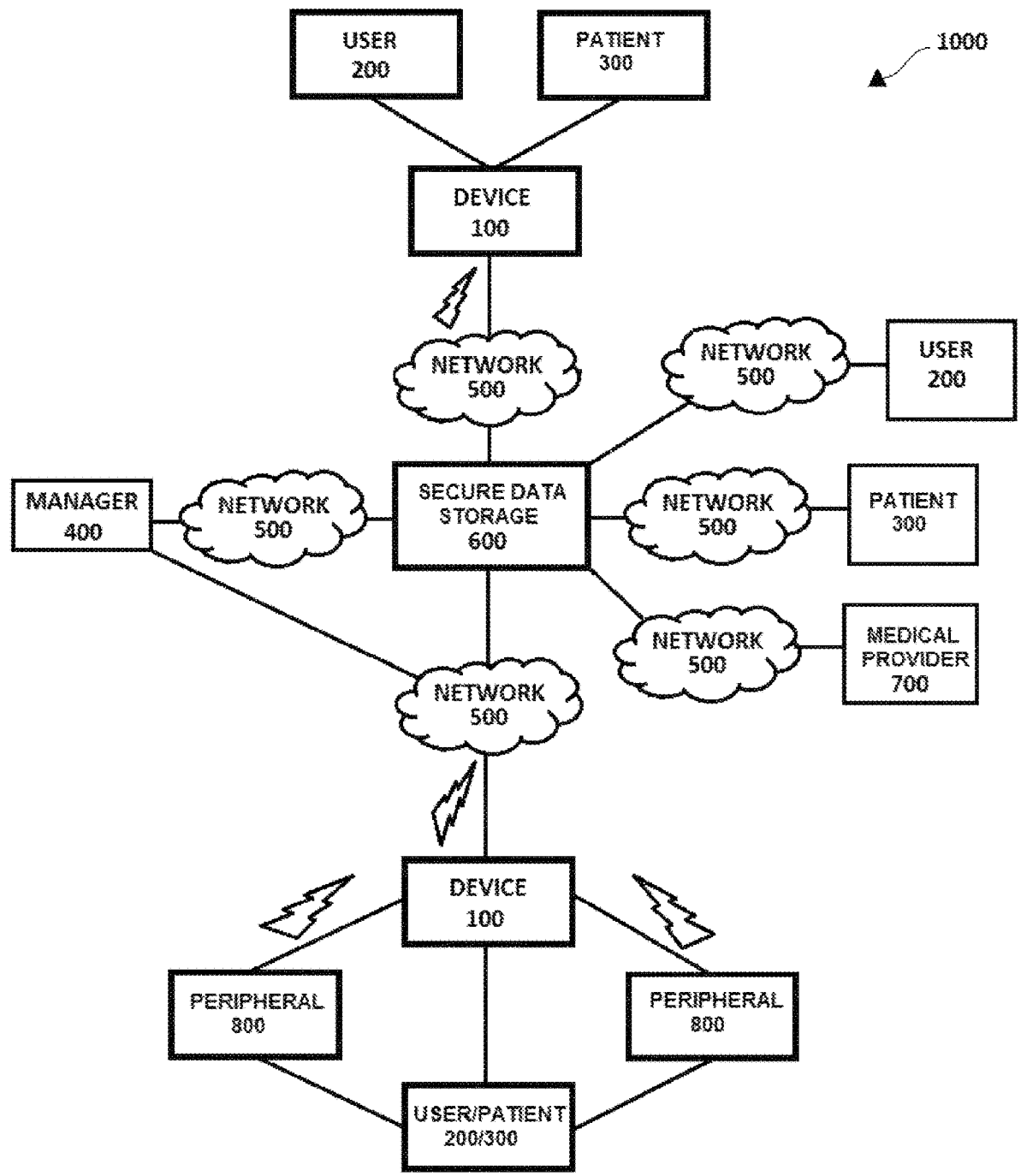
FIG. 5 is a diagram of an example system according to various example embodiments, depicting the example system operating in a third non-limiting example modality.

Turning to FIGS. 3, 4, and 5, in various example embodiments the mobile device 100 may be configured to automatically wirelessly communicate to a network 500 the data corresponding to the various physiological measurements described herein. The mobile device 100 may be configured to communicate with and display information from the Internet, as a typical smartphone. The mobile device 100 may be configured to wirelessly communicate an alert to the user, and optionally to someone located remotely from the user, such as a medical provider 700, when data corresponding to physiological measurements taken by the device 100 exceeds a predetermined threshold.

For example, with reference to FIG. 3, provided in various example embodiments is a system 1000 comprising a plurality of mobile devices 100 as described herein, for use with a plurality of patients 300 (each of which may or may not be the user 200 of the respective device 100), all in wireless communication with a remotely-located computer network 500 configured and managed by a manager 400 to securely receive, store, compile, and selectively display from secure data storage 600 a plurality of formats of data corresponding to the physiological measurements of the patients 300. Such displays may be accessed via the Internet via a secure web browser using a password, for example (as indicated by the three boxes marked USER 200, PATIENT 300, and MEDICAL PROVIDER 700 on the right side of the middle portion of FIG. 3). In certain example embodiments such displays can be accessed via the Internet using the device 100 (as indicated by the upper three boxes in FIG. 3 marked USER 200, PATIENT 300, and DEVICE 100). The formats may include a single-patient format where the data corresponding to the physiological measurements corresponds to a single one of the patients 300, such as a user-friendly vital sign "dashboard" graphical user interface showing status and trends for various physiological measurements of the patient 300, for instance as gauges, as depicted in the photographs in the '543 application. The formats may also include a multiple-patient format where the data corresponding to the physiological measurements corresponds to a plurality of the patients, for instance in a chart or spreadsheet form. Multiple patient data would be accessed by a medical provider 700, for example.

FIG. 4 depicts a use of the system 1000 where a single user 200 uses a single device 100 on multiple patients, for instance in the case of a traveling nurse or a caregiver in a facility. The mobile device 100 may be configured to be selectably operable in a plurality of modes appropriate for use by either one user/patient 200/300 or by one user 200 with multiple patients 300. For example, in a first mode the mobile device 100 may be configured to display on the display 118 visual indications of data corresponding to the physiological measurements described herein without communicating said data wirelessly to a network 500. In a second mode the mobile device 100 may be configured to display on the display 118 visual indications of data corresponding to the physiological measurements described herein and to associate with that data a patient identifier, time stamp, and GPS location, and to automatically wirelessly communicate that data for each patient securely to a network 500. In a third mode the mobile device 100 may be configured to display on the display 118 visual indications of data corresponding to the physiological measurements described herein and to automatically wirelessly communicate that data securely to a network 500. In such a third mode the mobile device 100 may be further configured to automatically wirelessly communicate securely to a network 500 data corresponding to physiological measurements taken by one or more peripheral devices 800 not physically connected to the mobile device 100. In a third mode the mobile device 100 may be configured to allow the patient 300 to communicate with remotely located persons, such a medical provider 700, by audio and video.

As depicted in FIG. 5, the mobile device 100 may be configured to wirelessly receive, display on display 118, and wirelessly communicate data corresponding to physiological measurements taken by a peripheral device 800 not physically connected to the mobile device 100, whether by a user 200 or patient 300. The peripheral devices 800 may include, for example, a scale configured to measure and wirelessly communicate data corresponding to the weight of the patient, for instance as depicted in the photographs in the '543 application. The peripheral devices 800 may include a fall detection device configured to be worn by the patient and to detect and to wirelessly communicate data indicating when the patient has fallen, for instance as described in U.S. Pat. No. 8,116,724 B2 to Peabody, entitled System Containing Location-Based Personal Emergency Response Device, issued Feb. 14, 2012 ("the '724 patent"), which is incorporated herein by reference. The peripheral devices 800 may include an activity tracker configured to be worn by the patient and to measure and wirelessly communicate data corresponding to an amount of physical activity engaged in by the patient over a period of time. Any other suitable peripheral device 800 may also be used. In certain example embodiments peripheral devices 800 can be used only in a certain mode or modes, while in other example embodiments peripheral devices 800 can be used in any modes.

Figure 6:
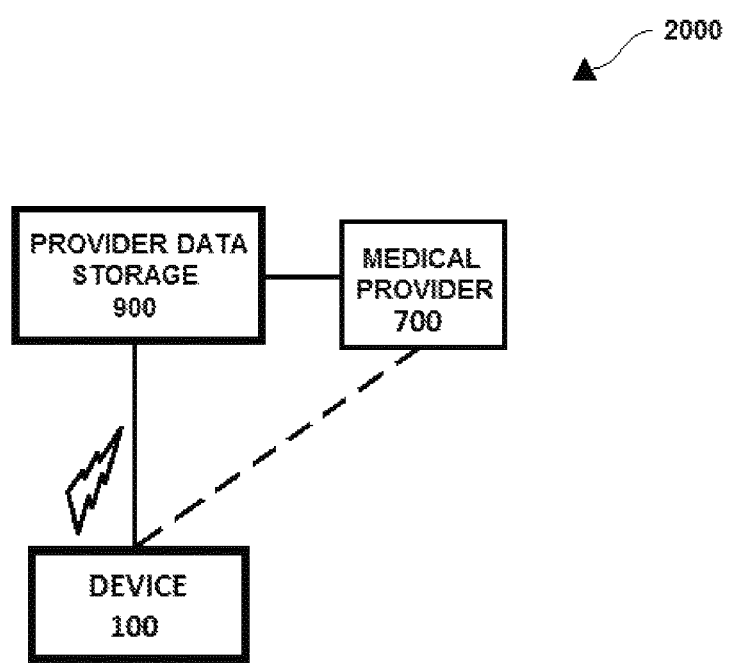
FIG. 6 is a diagram of an example system according to various example embodiments, depicting an example device communicating directly with a system of a healthcare provider.

Turning to FIG. 6, in any of the above modes or in different modes, an alternative system 2000 may be used where the device 100 wirelessly communicates data corresponding to physiological measurements directly to the provider's system 900, so that the medical provider 700 can access the data directly from their own secure system 900, such as a medical records system, without the data residing elsewhere on the cloud or on the servers of any other party. Provided are at least three ways to synchronize the device 100 directly with a provider's system 900. In a first option, provided is a simple API layer with a standard HL7 interface utilizing a point-of-care format through a provided database. In a second option, a simple unlock code may be provided that allows the provider 700 or the provider's system 900 to change the URL on the device 100 to point the URL to the provider's own web services or system 900. In a third option, an unlock code may be provided on the device 100 that allows the provider 700 or the provider's system 900 to load their own application or app to the device 100 for maximum control over the device 100.

Figure 7:
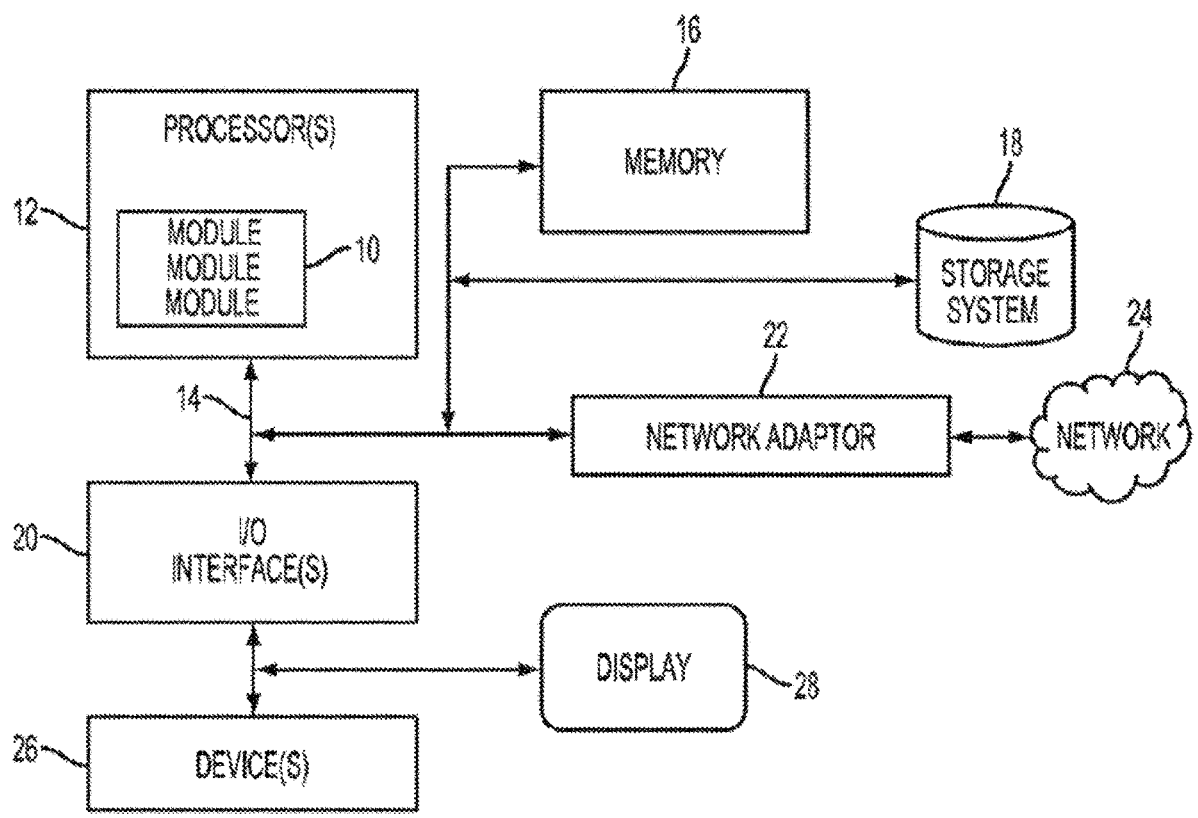
FIG. 7 is non-limiting diagram of various example components of a computer processing structure according to various example embodiments.

FIG. 7 illustrates a schematic of an example computer processing structure that may in certain example embodiments implement various aspects of the present disclosure. The computer processing structure is only one example of a suitable processing system and is not intended to suggest any limitation as to the scope of use or functionality of embodiments of the methodology described herein. The processing system shown may be operational with numerous other general purpose or special purpose computing system environments or configurations. Examples of well-known computing systems, environments, and/or configurations that may be suitable for use with the processing system shown in FIG. 7 may include, but are not limited to, personal computer processing structures, server computer processing structures, thin clients, thick clients, smart phones, tablets, handheld or laptop devices, multiprocessor systems, microprocessor-based systems, set top boxes, programmable consumer electronics, network PCs, minicomputer processing structures, mainframe computer processing structures, and distributed cloud computing environments that include any of the above systems or devices, and the like.

The computer processing structure may be described in the general context of a computer comprising executable instructions, such as program modules, being executed by a computer processing structure. Generally, program modules may include routines, programs, objects, components, logic, data structures, and so on that perform particular tasks or implement particular abstract data types. The computer processing structure may be practiced in distributed cloud computing environments where tasks are performed by remote processing devices that are linked through a communications network. In a distributed cloud computing environment, program modules may be located in both local and remote computer processing structure storage media including memory storage devices.

The components of computer processing structure may optionally include, but are not limited to, one or more processors or processing units 12, a system memory 16, and a bus 14 that couples various system components including system memory 16 to processor 12. The processor 12 may include one or more components of one or more data processing, calculating, formatting, and communicating modules 10 that perform the methods described herein. The modules 10 may be programmed into the integrated circuits of the processor 12, or loaded from memory 16, storage device 18, or network 24 or combinations thereof.

Bus 14 may represent one or more of any of several types of bus structures, including a memory bus or memory controller, a peripheral bus, an accelerated graphics port, and a processor or local bus using any of a variety of bus architectures. By way of example, and not limitation, such architectures include Industry Standard Architecture (ISA) bus, Micro Channel Architecture (MCA) bus, Enhanced ISA (EISA) bus, Video Electronics Standards Association (VESA) local bus, and Peripheral Component Interconnects (PCI) bus.

Computer processing structure may include a variety of computer processing structure readable media. Such media may be any available media that is accessible by computer processing structure, and it may include both volatile and non-volatile media, removable and non-removable media.

System memory 16 can include computer processing structure readable media in the form of volatile memory, such as random access memory (RAM) and/or cache memory or others. Computer processing structure may further include other removable/non-removable, volatile/non-volatile computer processing structure storage media. By way of example only, storage system 18 can be provided for reading from and writing to a non-removable, non-volatile magnetic media (e.g., a "hard drive"). Although not shown, a magnetic disk drive for reading from and writing to a removable, non-volatile magnetic disk (e.g., a "floppy disk"), and an optical disk drive for reading from or writing to a removable, non-volatile optical disk such as a CD-ROM, DVD-ROM or other optical media can be provided. In such instances, each can be connected to bus 14 by one or more data media interfaces.

Computer processing structure may also communicate with one or more external devices 26 such as a keyboard, a pointing device, a display 28, etc.; one or more devices that enable a user to interact with computer processing structure; and/or any devices (e.g., network card, modem, etc.) that enable computer processing structure to communicate with one or more other computing devices. Such communication can occur via Input/Output (I/O) interfaces 20.

Still yet, computer processing structure can communicate with one or more networks 24 such as a local area network (LAN), a general wide area network (WAN), and/or a public network (e.g., the Internet) via network adapter 22. As depicted, network adapter 22 communicates with the other components of computer processing structure via bus 14. It should be understood that although not shown, other hardware and/or software components could be used in conjunction with computer processing structure. Examples include, but are not limited to: microcode, device drivers, redundant processing units, external disk drive arrays, RAID systems, tape drives, and data archival storage systems, etc.

As will be appreciated by one skilled in the art, aspects of the present invention may be embodied as a system, method or computer program product. Accordingly, aspects of the present invention may take the form of an entirely hardware embodiment, an entirely software embodiment (including firmware, resident software, micro-code, etc.) or an embodiment combining software and hardware aspects that may all generally be referred to herein as a "circuit," "module" or "system." Furthermore, aspects of the present invention may take the form of a computer program product embodied in one or more computer readable medium(s) having computer readable program code embodied thereon.

Any combination of one or more computer readable medium(s) may be utilized. The computer readable medium may be a computer readable signal medium or a computer readable storage medium. A computer readable storage medium may be, for example, but not limited to, an electronic, magnetic, optical, electromagnetic, infrared, or semiconductor system, apparatus, or device, or any suitable combination of the foregoing. More specific examples (a non-exhaustive list) of the computer readable storage medium would include the following: an electrical connection having one or more wires, a portable computer diskette, a hard disk, a random access memory (RAM), a read-only memory (ROM), an erasable programmable read-only memory (EPROM or Flash memory), an optical fiber, a portable compact disc read-only memory (CD-ROM), an optical storage device, a magnetic storage device, or any suitable combination of the foregoing. In the context of this document, a computer readable storage medium may be any tangible medium that can contain, or store a program for use by or in connection with an instruction execution system, apparatus, or device.

A computer readable signal medium may include a propagated data signal with computer readable program code embodied therein, for example, in baseband or as part of a carrier wave. Such a propagated signal may take any of a variety of forms, including, but not limited to, electromagnetic, optical, or any suitable combination thereof. A computer readable signal medium may be any computer readable medium that is not a computer readable storage medium and that can communicate, propagate, or transport a program for use by or in connection with an instruction execution system, apparatus, or device.

Program code embodied on a computer readable medium may be transmitted using any appropriate medium, including but not limited to wireless, wireline, optical fiber cable, RF, etc., or any suitable combination of the foregoing.

Computer program code for carrying out operations for aspects of the present invention may be written in any combination of one or more programming languages, including an object oriented programming language such as Java, Smalltalk, C++ or the like and conventional procedural programming languages, such as the "C" programming language or similar programming languages, a scripting language such as Perl, VBS or similar languages, and/or functional languages such as Lisp and ML and logic-oriented languages such as Prolog. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider).

Aspects of the present invention are described with reference to flowchart illustrations and/or block diagrams of methods, apparatus (systems) and computer program products according to embodiments of the invention. It will be understood that each block of the flowchart illustrations and/or block diagrams, and combinations of blocks in the flowchart illustrations and/or block diagrams, can be implemented by computer program instructions. These computer program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks.

These computer program instructions may also be stored in a computer readable medium that can direct a computer, other programmable data processing apparatus, or other devices to function in a particular manner, such that the instructions stored in the computer readable medium produce an article of manufacture including instructions which implement the function/act specified in the flowchart and/or block diagram block or blocks.

The computer program instructions may also be loaded onto a computer, other programmable data processing apparatus, or other devices to cause a series of operational steps to be performed on the computer, other programmable apparatus or other devices to produce a computer implemented process such that the instructions which execute on the computer or other programmable apparatus provide processes for implementing the functions/acts specified in the flowchart and/or block diagram block or blocks.

The flowchart and block diagrams in the figures illustrate the architecture, functionality, and operation of possible implementations of systems, methods and computer program products according to various example embodiments of the present invention. In this regard, each block in the flowchart or block diagrams may represent a module, segment, or portion of code, which comprises one or more executable instructions for implementing the specified logical function(s). It should also be noted that, in some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts, or combinations of special purpose hardware and computer instructions.

The computer program product may comprise all the respective features enabling the implementation of the methodology described herein, and which—when loaded in a computer processing structure—is able to carry out the methods. Computer program, software program, program, or software, in the present context means any expression, in any language, code or notation, of a set of instructions intended to cause a system having an information processing capability to perform a particular function either directly or after either or both of the following: (a) conversion to another language, code or notation; and/or (b) reproduction in a different material form.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

The corresponding structures, materials, acts, and equivalents of all means or step plus function elements, if any, in the claims below are intended to include any structure, material, or act for performing the function in combination with other claimed elements as specifically claimed. The description of the present invention has been presented for purposes of illustration and description, but is not intended to be exhaustive or limited to the invention in the form disclosed. Many modifications and variations will be apparent to those of ordinary skill in the art without departing from the scope and spirit of the invention. The embodiment was chosen and described in order to best explain the principles of the invention and the practical application, and to enable others of ordinary skill in the art to understand the invention for various embodiments with various modifications as are suited to the particular use contemplated.

Various aspects of the present disclosure may be embodied as a program, software, or computer instructions embodied in a computer or machine usable or readable medium, which causes the computer or machine to perform the steps of the method when executed on the computer, processor, and/or machine. A program storage device readable by a machine, tangibly embodying a program of instructions executable by the machine to perform various functionalities and methods described in the present disclosure is also provided.

The system and method of the present disclosure may be implemented and run on a general-purpose computer or special-purpose computer processing structure. The terms "computer processing structure" and "computer network" as may be used in the present application may include a variety of combinations of fixed and/or portable computer hardware, software, peripherals, and storage devices. The computer processing structure may include a plurality of individual components that are networked or otherwise linked to perform collaboratively, or may include one or more stand-alone components. The hardware and software components of the computer processing structure of the present application may include and may be included within fixed and portable devices such as desktop, laptop, and/or server. A module may be a component of a device, software, program, or system that implements some "functionality", which can be embodied as software, hardware, firmware, electronic circuitry, or the like.

Any of the suitable technologies set forth and incorporated herein may be used to implement various example aspects of the invention as would be apparent to one of skill in the art.

Although exemplary embodiments and applications of the invention have been described herein including as described above and shown in the included example Figures, there is no intention that the invention be limited to these exemplary embodiments and applications or to the manner in which the exemplary embodiments and applications operate or are described herein. Indeed, many variations and modifications to the exemplary embodiments are possible as would be apparent to a person of ordinary skill in the art. The invention may include any device, structure, method, or functionality, as long as the resulting device, system or method falls within the scope of one of the claims that are allowed by the patent office based on this or any related patent application.

What is claimed is:

1. A mechanical blood pressure measuring kit, comprising:
    a mobile device integrated in a body having four radiused outer corners that is small enough to fit in the palm of a user's hand, the mobile device configured to take a plurality of physiological measurements of a patient, including electrocardiographic measurements, blood oxygen saturation level measurements, pulse rate measurements, body temperature measurements, blood pressure measurements when connected with a removable inflatable arm cuff, and blood glucose measurements when connected with an elongated test strip having at a first end an electrical connection point and at a second end an electrochemical cell, and to display and wirelessly communicate data corresponding to said physiological measurements, the mobile device comprising:
        a display;
        a processor;
        a wireless modem with mobile broadband and GPS functionality;
        a power source;
        two or more electrocardiographic electrodes integrated with and positioned on the body of the mobile device and configured to measure electrocardiographic signals of the patient when gripped by fingers or thumbs of the patient;
        a fingertip pulse oximeter formed into the body of the mobile device between two of the four radiused outer corners and configured to measure pulse rate and blood oxygen saturation levels of the patient when a tip of a finger of the patient is inserted therein;
        a temperature sensor integrated with and positioned on the body of the mobile device and configured to measure body temperature of the patient when the temperature sensor is placed against the patient's skin;
        a blood pressure measuring structure within the body of the mobile device, comprising a controller, motor, pressure sensor, and pump in air communication with a tube interface at the body that is adapted to be removably and sealably connected with an inflatable arm cuff; and
        a blood glucose measuring structure within the body of the mobile device, comprising an electrical connector at the body, the electrical connector disposed to form an electrical connection with the electrical connection point on the first end of the elongated test strip, when the elongated strip is inserted in the electrical connector; and an inflatable arm cuff comprising a clip structure attached directly to an outer surface of the inflatable arm cuff, the clip structure sized and shaped to removably connect the mobile device to the inflatable arm cuff and comprising curved resilient projections extending away from the inflatable arm cuff that are sized and shaped to snap on to the four radiused outer corners of the mobile device, the clip structure further comprising a fitting that is configured and positioned to removably and sealably attach to the tube interface on the mobile device so that the pump is in air flow and air pressure communication with the inflatable arm cuff when the mobile device is removably connected to the inflatable arm cuff with the clip structure.

2. The mechanical blood pressure measuring kit of claim 1, wherein the mobile device is configured to automatically wirelessly communicate to a network said data corresponding to said physiological measurements.

3. The mechanical blood pressure measuring kit of claim 1, wherein the mobile device comprises a touch-screen data input structure and is configured to manually receive, display, and wirelessly communicate data corresponding to physiological measurements of the patient that were manually taken.

4. The mechanical blood pressure measuring kit of claim 1, wherein the mobile device is configured to wirelessly receive, display, and wirelessly communicate data corresponding to physiological measurements taken by a peripheral device not physically connected to the mobile device.

5. The mechanical blood pressure measuring kit of claim 4, wherein the peripheral device is selected from the group consisting of:
  a scale configured to measure and wirelessly communicate data corresponding to the weight of the patient;
  a fall detection device configured to be worn by the patient and to detect and to wirelessly communicate data indicating when the patient has fallen; and
  an activity tracker configured to be worn by the patient and to measure and wirelessly communicate data corresponding to an amount of physical activity engaged in by the patient over a period of time.

6. The mechanical blood pressure measuring kit of claim 1, wherein the mobile device further comprises a cellular telephone.

7. The mechanical blood pressure measuring kit of claim 6, wherein the mobile device is configured to communicate with and display information from the Internet.

8. The mechanical blood pressure measuring kit of claim 7, wherein the mobile device comprises a camera, microphone, and speaker, and is configured to allow the user to video-conference with one or more remotely-located persons.

9. The mechanical blood pressure measuring kit of claim 1, wherein the mobile device is further configured to communicate an alert when said data corresponding to said physiological measurements exceeds a predetermined threshold.

10. The mechanical blood pressure measuring kit of claim 9, wherein the mobile device is configured to communicate an alert to the user when said data corresponding to said physiological measurements exceeds a predetermined threshold.

11. The mechanical blood pressure measuring kit of claim 9, wherein the mobile device is configured to wirelessly communicate an alert to someone located remotely from the user when said data corresponding to said physiological measurements exceeds a predetermined threshold.

12. The mechanical blood pressure measuring kit of claim 1, further configured to be selectably operable in a plurality of modes, wherein:
  in a first mode the mobile device is configured to display visual indications of data corresponding to said physiological measurements without communicating said data wirelessly; and
  in a second mode the mobile device is configured to display visual indications of data corresponding to said physiological measurements and to associate with said data: a patient identifier; time stamp; and GPS location; and to automatically wirelessly communicate said data for each patient securely to a network.

13. The mechanical blood pressure measuring kit of claim 1, wherein:
  the mobile device is configured to display visual indications of data corresponding to said physiological measurements and to automatically wirelessly communicate said data securely to a network.

14. The mechanical blood pressure measuring kit of claim 13, wherein the mobile device is configured to wirelessly receive, display, and wirelessly communicate data corresponding to physiological measurements taken by a peripheral device not physically connected to the mobile device, and the mobile device is configured to automatically wirelessly communicate securely to a network the data corresponding to the physiological measurements taken by the peripheral device not physically connected to the mobile device.

15. The mechanical blood pressure measuring kit of claim 13, wherein the mobile device comprises a built-in camera, microphone, and speaker, and is configured to wirelessly communicate audio and video signals, to play audio, and to display video, and the mobile device is configured to allow the patient to communicate with remotely located persons by audio and video.

16. A system comprising:
  a plurality of mechanical blood pressure measuring kits according to claim 1 for use with a plurality of patients, in wireless communication with a remotely-located computer network configured to securely receive, store, compile, and selectively display in a plurality of formats said data corresponding to said physiological measurements of said patients.

17. The system of claim 16, wherein the plurality of formats are selected from the group consisting of:
  a single-patient format where said data corresponding to said physiological measurements corresponds to a single one of said patients; and
  a multiple-patient format where said data corresponding to said physiological measurements corresponds to a plurality of said patients.

18. A mechanical blood pressure measuring kit, comprising:
  a mobile device integrated in a body having four radiused outer corners that is small enough to fit in the palm of a user's hand, the mobile device configured to take a plurality of physiological measurements of a patient, including electrocardiographic measurements, blood oxygen saturation level measurements, pulse rate measurements, body temperature measurements, blood pressure measurements when connected with a removable inflatable arm cuff, and blood glucose measurements when connected with an elongated test strip having at a first end an electrical connection point and at a second end an electrochemical cell, and to display and wirelessly communicate data corresponding to said physiological measurements, the mobile device comprising:

a display;
a processor;
a wireless modem with mobile broadband and GPS functionality;
a power source;
a touch-screen data input structure and is configured to manually receive, display, and wirelessly communicate data corresponding to physiological measurements of the patient that were manually taken;
a cellular telephone;
a camera, microphone, and speaker, all configured to allow the user to video-conference with one or more remotely-located persons;
two or more electrocardiographic electrodes integrated with and positioned on the body of the mobile device and configured to measure electrocardiographic signals of the patient when gripped by fingers or thumbs of the patient;
a fingertip pulse oximeter formed into the body of the mobile device between two of the four radiused outer corners and configured to measure pulse rate and blood oxygen saturation levels of the patient when a tip of a finger of the patient is inserted therein;
a temperature sensor integrated with and positioned on the body of the mobile device and configured to measure body temperature of the patient when the temperature sensor is placed against the patient's skin;
a blood pressure measuring structure within the body of the mobile device, comprising a controller, motor, pressure sensor, and pump in air communication with a tube interface at the body that is adapted to be removably and sealably connected with an inflatable arm cuff; and
a blood glucose measuring structure within the body of the mobile device, comprising an electrical connector at the body, the electrical connector disposed to form an electrical connection with the electrical connection point on the first end of the elongated test strip, when the elongated strip is inserted in the electrical connector; and an inflatable arm cuff comprising a clip structure attached directly to an outer surface of the inflatable arm cuff, the clip structure sized and shaped to removably connect the mobile device to the inflatable arm cuff and comprising curved resilient projections extending away from the inflatable arm cuff that are sized and shaped to snap on to the four radiused outer corners of the mobile device, the clip structure further comprising a fitting that is configured and positioned to removably and sealably attach to the tube interface on the mobile device so that the pump is in air flow and air pressure communication with the inflatable arm cuff when the mobile device is removably connected to the inflatable arm cuff with the clip structure;

wherein the mobile device is configured to:
automatically wirelessly communicate to a network said data corresponding to said physiological measurements;
wirelessly receive, display, and wirelessly communicate data corresponding to physiological measurements taken by a peripheral device not physically connected to the mobile device, wherein the peripheral device is selected from the group consisting of: a scale configured to measure and wirelessly communicate data corresponding to the weight of the patient; a fall detection device configured to be worn by the patient and to detect and to wirelessly communicate data indicating when the patient has fallen; and an activity tracker configured to be worn by the patient and to measure and wirelessly communicate data corresponding to an amount of physical activity engaged in by the patient over a period of time;
communicate with and display information from the Internet;
wirelessly communicate an alert to the user and to someone located remotely from the user when said data corresponding to said physiological measurements exceeds a predetermined threshold; and
be selectably operable in a plurality of modes, wherein in at least one mode the mobile device is configured to display visual indications of data corresponding to said physiological measurements and to associate with said data: a patient identifier; time stamp; and GPS location; and to automatically wirelessly communicate said data for each patient securely to a network.

* * * * *